(12) United States Patent
Asif-Rosenberg et al.

(10) Patent No.: US 11,749,385 B2
(45) Date of Patent: Sep. 5, 2023

(54) HAND HYGIENE SYSTEM AND METHOD

(71) Applicants: Ayelet Asif-Rosenberg, Shoham (IL);
Nir Rosenberg, Shoham (IL)

(72) Inventors: Ayelet Asif-Rosenberg, Shoham (IL);
Nir Rosenberg, Shoham (IL)

( * ) Notice: Subject to any disclaimer, the term of this patent is extended or adjusted under 35 U.S.C. 154(b) by 791 days.

(21) Appl. No.: 16/503,829

(22) Filed: Jul. 5, 2019

(65) Prior Publication Data

US 2021/0005291 A1   Jan. 7, 2021

(51) Int. Cl.
| | | |
|---|---|---|
| *G16H 10/60* | (2018.01) | |
| *G16H 40/20* | (2018.01) | |
| *G16H 15/00* | (2018.01) | |
| *G06K 7/14* | (2006.01) | |
| *G08B 21/24* | (2006.01) | |
| *G08B 21/18* | (2006.01) | |
| *A61L 2/24* | (2006.01) | |
| *A61L 2/00* | (2006.01) | |

(52) U.S. Cl.
CPC .......... *G16H 10/60* (2018.01); *A61L 2/0082* (2013.01); *A61L 2/24* (2013.01); *G06K 7/1413* (2013.01); *G08B 21/182* (2013.01); *G08B 21/245* (2013.01); *G16H 40/20* (2018.01); *A61L 2202/14* (2013.01)

(58) Field of Classification Search
CPC ...... G16H 10/60; G16H 40/20; A61L 2/0082; A61L 2/24; A61L 2202/14; G06K 7/1413; G08B 21/182; G08B 21/245
See application file for complete search history.

(56) References Cited

U.S. PATENT DOCUMENTS

2012/0187146 A1\*  7/2012  Chopra ............... A61L 2/16
                                                          222/23
2015/0134357 A1    5/2015  Davis et al.

OTHER PUBLICATIONS

Digital signage smart integrated hand sanitizer. (Nov. 22, 2018). [Video]. YouTube. https://www.youtube.com/watch?v=1oGxfDCymx0 (Year: 2018).\*

\* cited by examiner

*Primary Examiner* — Michael Tomaszewski
*Assistant Examiner* — Mohmad Muqueeth
(74) *Attorney, Agent, or Firm* — Browdy and Neimark, PLLC

(57) ABSTRACT

The present invention provides a hand hygiene system implemented on a computer comprising:
a health management program including a cleaning hand module implemented on said computer; and
a sanitizer dispenser equipped with a sensor that is connected to said computer;
wherein every time the dispenser is used, the computer receives a signal indicating that the dispenser was used, and
wherein said health management program entails access to a new/consequent patient file only when receiving said signal,
whereby said hand hygiene system makes the performance of hand hygiene an obligatory action in between patients.

12 Claims, 7 Drawing Sheets

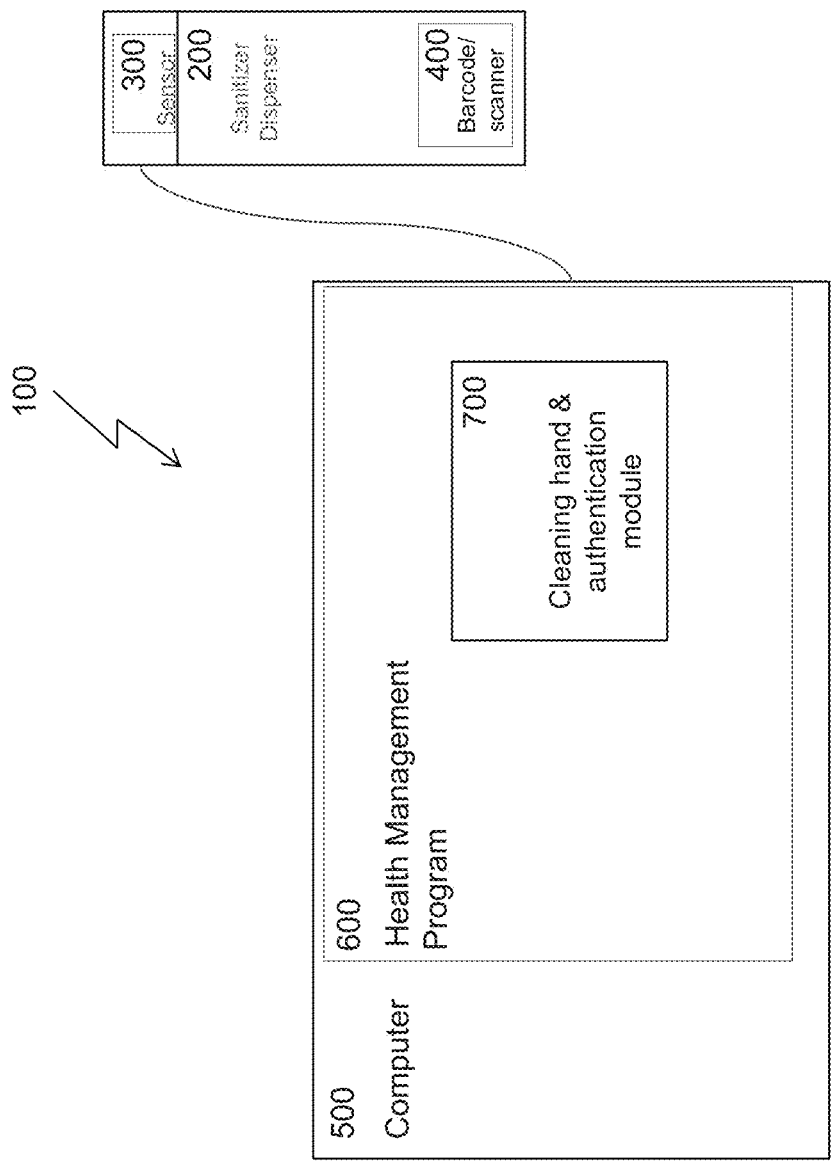

Cleaning Hands & Authentication Module 700

Upon receiving indication of a user trying to access a new patient file for writing new data, asking the user to cleanse his/her hands using sanitizer dispenser 200 that is connected to the computer.
710

When receiving a signal detected by sensor 200 upon using sanitizer dispenser 200, and upon authentication of said signal, enabling the user to get an access to a new/consequent patient data file.
720

Authenticating of said signal may include authenticating dispenser barcode or sensor ID number.
730

Increasing counter which indicates number of times of using the sanitizer dispenser 102 (i.e., the number of times pushing the lever, the number of times the motor is operated when sensing the presence of a hand below the dispenser etc..). When the counter is above a predefined threshold, alerting the user to replace the dispenser, after replacing the dispenser reading barcode on new dispenser or receiving identification code of the dispenser sensor.
740

Fig. 3

Health management software 600

Receiving indication from either cleaning hands & authentication module 700 or sensor 300 that the sanitizer disperser was in use.
610

Enabling to switch between patient records or starting or ending session of patient record.
620

User updating information on patient file on the electronic device.
630

Fig. 4

HAND HYGIENE SYSTEM AND METHOD

FIELD OF THE INVENTION

The present invention relates to hand hygiene systems and methods. More specifically, the present invention relates to a system and method for monitoring and controlling hand hygiene.

BACKGROUND OF THE INVENTION

Health care-associated infections (HAIs) is a very prevalent and serious problem among patients. The occurrence of HAIs continues to escalate at an alarming rate. HAIs originally referred to those infections associated with admission in an acute-care hospital (formerly called a nosocomial infection), but the term now applies to any infection acquired in the continuum of setting where persons receive health care (e.g., long-term care, home care, ambulatory care). These unanticipated infections develop during the course of health care treatment and result in significant patient morbidity and mortality; prolong the duration of hospital stays; and necessitates additional diagnostic and therapeutic interventions, which generate added costs to those already incurred by the patient underlying disease.

HAIs are considered an undesirable outcome, and at some are preventable. They are considered and indicator of the quality of patient care, and adverse event, and a patient safety issue.

A very disturbing fact is that although the number of hospitalizations and the average duration of inpatient admissions have decreased, the frequency of HAIs has increased.

The true incidence of HAIs is likely to be underestimated as hospital stays may be shorter than the incubation period of the infecting microorganism (a developing infection), and symptoms may not manifest until days after patient discharge.

The most important and frequent mode of microorganisms transmission in the health care setting is contact transmission. Organisms are transferred through direct contact between an infected or colonized patient and a health care worker or another patient. A health care worker can transfer the infecting organism residing on his skin to a susceptible patient who develops an infection from that organism. This is called an indirect contact route of transmission from on patient to another. Microorganisms that can be spread by contact include many of the antibiotic-resistant organisms.

Epidemiological studies continue to demonstrate the favorable cost-benefit ratio and positive effects of performing hand hygiene, including hand washing and alcohol-based hand rubs, in preventing transmission of pathogens in health-care facilities.

Although the clear benefits of hand hygiene have been proven in multiple settings, the lack of consistent hand-washing practices remains a worldwide issue. The major problem in the compliance to perform regular and consistent hand hygiene originates from the voluntary rather than obligatory nature of this important task.

The Center for Disease Control (CDC) defined 5 important moments to perform hand hygiene, 3 of them during regular patient care.

SUMMARY OF THE INVENTION

The time interval between taking care of two patients is the most important in preventing transmission of pathogens from one patient to another.

In modern health care service, this interval is usually being utilized for patient's data recording using computerized health-care program. This data recording is done by both medical and nursing staff. The computers are positioned on mobile carts in the hospitals' departments and on the physician or nurse's desk in the ambulatory setting.

Performing hand hygiene before entering the patient's data and before touching the next patient will reduce transmission of pathogens from one patient, through the health-care provider, to the next patient.

Thus, a system and method in accordance with some embodiments of the present invention make the performance of hand hygiene an obligatory action in between patients.

In accordance with some embodiments of the present invention, there is provided a hand hygiene system comprising:

a health management program including a cleaning hand module implemented on a processor; and a sanitizer dispenser equipped with a sensing unit that is associated with said processor via wired communication or wireless communication;

wherein the sensing unit is configured to identify every time the dispenser is used and to transmit a signal to the health management program, and wherein said health management program provides access to a new/consequent patient file only when receiving said signal.

Furthermore, according to some embodiments of the present invention, the sensing unit comprises one of a touch sensor, a motion sensor, a sound sensor, an acoustic sensor and an electrical or magnetic switch.

Furthermore, according to some embodiments of the present invention, the health management program pops-up a window notifying that said sanitizer dispenser must be used prior to opening a new patient's file.

Furthermore, according to some embodiments of the present invention, the health management program closes said window and opens a new medical file when receiving a signal from said sensing unit.

Furthermore, according to some embodiments of the present invention, the health management program maintains an open new file button unresponsive until receiving a signal from said sensing unit indicating that the sanitizer dispenser is used.

Furthermore, according to some embodiments of the present invention, the sanitizer dispenser further comprising identification means selected from a barcode or a scanner.

Furthermore, according to some embodiments of the present invention, the sanitizer dispenser further comprises a module that includes an increasing counter indicating the number of times of using the sanitizer dispenser.

Furthermore, according to some embodiments of the present invention, when said counter is above a predefined threshold, the module provides an alert to replace the dispenser, and when said dispenser is replaced, said counter starts over.

Furthermore, according to some embodiments of the present invention, the sanitizer dispenser comprises (a) a reservoir to hold a sanitizer and (b) a dispensing mechanism selected from a mechanical, electrical, or mechanical-electrical dispensing mechanism.

Furthermore, according to some embodiments of the present invention, there is also provided a method implemented on a processor for using the hand hygiene system described above. The method is and comprises the steps of:

receiving an indication from a health management program that a user is trying to access a new/consequent patient file;

sending request to the user to cleanse his/her hands using a sanitizer dispenser;

in case of detecting the activation of said sanitizer dispenser, transferring a signal to said processor; and recognizing the signal and opening the medical file of a new/consequent patient.

Furthermore, according to some embodiments of the present invention, there is also provided a method implemented on a processor of a public remote computer for using the hand hygiene system described above. The method is and comprises the steps of: receiving an indication from a health management program that a user is trying to access a new/consequent patient file;

sending request to the user to identify himself/herself and to cleanse his/her hands using a sanitizer dispenser;

in case of detecting the activation of said sanitizer dispenser and identifying the user, transferring a signal to the processor of the accompanied public computer, and recognizing the signal and opening the medical file of a new/consequent patient.

Furthermore, according to some embodiments of the present invention, the above method comprises sending request to the user to identify his/herself via identification means selected from a barcode or a scanner prior to activating said sanitizer dispenser.

Furthermore, according to some embodiments of the present invention, the above methods comprising maintaining an open new file button unresponsive and/or popping up a window notifying that a sanitizer dispenser must be used prior to opening a new/consequent patient's file.

Furthermore, according to some embodiments of the present invention, the above methods further comprising implementing a counter in said sanitizer dispenser for indicating the number of times of using the sanitizer dispenser.

Furthermore, according to some embodiments of the present invention, the above methods further comprising providing an alert to replace the dispenser when said counter above a predefined threshold.

BRIEF DESCRIPTION OF THE FIGURES

FIG. 1A provides a first hand-hygiene system for controlling hand hygiene of one or more health-care providers;

FIG. 3 shows a cleaning hands and authentication module in accordance with some embodiments of the present invention;

FIG. 4 shows health management software in accordance with some embodiments of the present invention.

DETAILED DESCRIPTION OF THE FIGURES

Figure 1B:
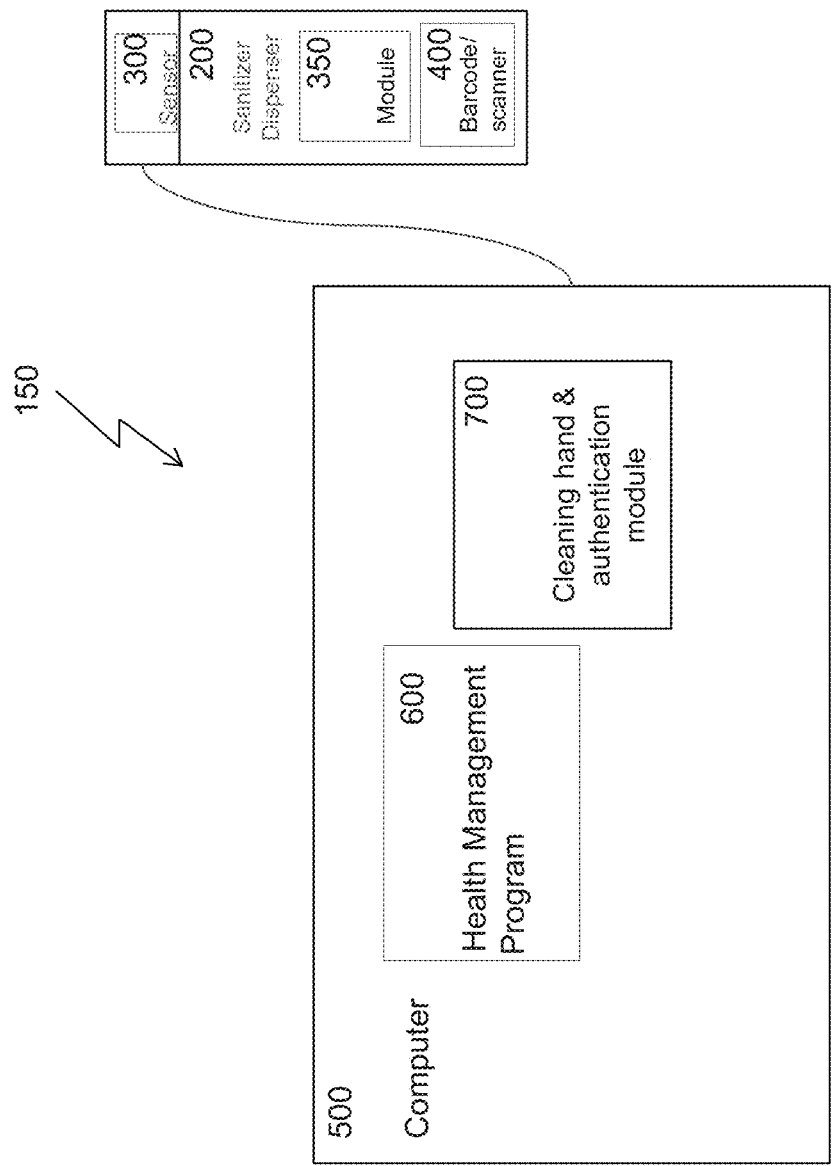
FIG. 1B provides a second hand-hygiene system for controlling hand hygiene in accordance with other embodiments of the present invention.

FIG. 1A provides a first hand-hygiene system 100 for controlling hand hygiene of one or more health-care providers such as physicians, nurses or other healthcare personnel when treating patients in accordance with some embodiments of the present invention.

Hand-hygiene system 100 of the present invention makes the performance of hand hygiene an obligatory action in between patients.

Hand-hygiene system 100 comprises a sanitizer dispenser 200 equipped with a sensing unit/a miniature Arduino-based micro-controller 300, and a computer (a processor and associated memory) 500 equipped with a health management program 600 with a cleaning hand & authentication module 700.

Sensing unit 300 is associated with computer 500 via wired communication or wireless communication.

Hand-hygiene system 100 may further include identification means 400 such as a barcode or a scanner.

In accordance with some embodiments of the present invention, every time the dispenser is being used, the computer receives a signal, indicating that the dispenser is used.

In accordance with some embodiments of the present invention, an existing medical file program 600 may be modified to include a cleaning hand & authentication module 700, and thus, to include commands for conditioning access to a new patient file with the use of a sanitizer dispenser 200. For instance, the medical file program 600 may be modified to pop-up a window that notifies the user that he/she has to sanitize his/her hands in order to proceed and open a new patient's file. Upon receiving a signal from sanitizer dispenser 200, such notification window will close and the software may continue with opening of the new medical file only.

Alternatively, the medical file program may be modified to keep the open new file button unresponsive until the software recognizes a signal from sanitizer dispenser 200.

In accordance with some embodiments of the present invention, module 700 may be either implemented in health management program 600 or compiled separately as illustrated and described in FIG. 1B.

FIG. 1B provides a second hand-hygiene system 150 for controlling hand hygiene in accordance with other embodiments of the present invention. Hand-hygiene system 150 comprises a sanitizer dispenser 200 equipped with a sensing unit 300, health management program 600, and cleaning hand & authentication module 700. Sanitizer dispenser 200 may further include identification means 400 such as a barcode or a scanner and/or a module 350 which may include an increasing counter indicating number of times of using the sanitizer dispenser 200 (i.e., the number of times pushing the lever, the number of times the motor is operated when sensing the presence of a hand below the dispenser etc.).

In accordance with some embodiments of the present invention, sanitizer dispenser 200 may include a module 350 including an increasing counter which indicates number of times of using the sanitizer dispenser 200 (i.e., the number of time pushing the lever, the number of times the motor is operated when sensing the presence of a hand below the dispenser etc.). When the counter is above a predefined threshold, the user is alerted to replace the dispenser, and after replacing the dispenser, the counter starts over.

In accordance with some embodiments of the present invention, first hand-hygiene system 100 and second hand-hygiene system 150 ensure, to a certain extent, that health management program 600 may only use sanitizer dispenser 200.

In accordance with some embodiments of the present invention, when the physician/nurse opens a new patient's file (pressing the "open new file" button), the software pops-up a window notifying the physician/nurse to sanitize his/her hands by using the dispenser. Only after pressing the pump of the dispenser, this notification window will close and the software can continue with opening of the new medical file. In addition, an open new file button is unresponsive (disabled) until after the software recognizes a press on the dispenser.

In accordance with some embodiments of the present invention, sanitizer dispenser 200 may include a module 350 as seen in FIG. 1B. Module 350 may include an increasing counter which indicates the number of times of using the sanitizer dispenser 200 (i.e., the number of time pushing the lever, the number of times the motor is operated when sensing the presence of a hand below the dispenser etc.). When the counter is above a predefined threshold, the user is alerted to replace the dispenser.

Thus, in accordance with some embodiments, the present invention enables the integration of a medical file program (health software) with a sensor unit of the dispenser by combining a software component (e.g., driver) related to a dispenser sensor within the program. Once the driver is incorporated, the file management application may be able to detect the operation of the connected dispenser, at the correct stage, i.e., the stage of entering a new patient file.

As noted earlier, after selecting a patient file, the "Open" button may be in a disabled state, so that the user cannot press it. In addition, the application may provide a notification informing the user that he/she has to use the dispenser. When the application detects that the dispenser is used, the "Open" button changes to an enabled state and the user is able to press it and open the file.

To implement the above, the software may be updated by referencing the dispenser's driver (A Microsoft Windows DLL file) and using its API (Application Programming Interface). When the application starts-up, it initializes the driver, and registers with the driver to receive a software event when the dispenser is used (pressed). Then, the software is able to detect the point in time at which the dispenser is used and may consider such event whenever the user needs to open a new patient file. Thus, a dispenser usage is identified via a dispenser sensor software source files installed in the dispenser module 350, such software source files include the following:

Adding a reference record of the dispenser to the driver of the module 350 (The reference record may be in the form of a DLL file).

Initializing the driver, which establishes communication with the dispensers' hardware, recognizes the existence of the hardware and its connection to the computer, and monitors the pressing on the dispenser.

A programming event is initiated by the driver in order to identify a pressing event on the dispenser.

In accordance with some embodiments of the present invention, sanitizer dispenser 200 includes a reservoir to hold the sanitizer and a dispensing mechanism, i.e., a mechanical, electrical, or mechanical-electrical device for the purpose of dispensing a sanitizer.

Figure 2:
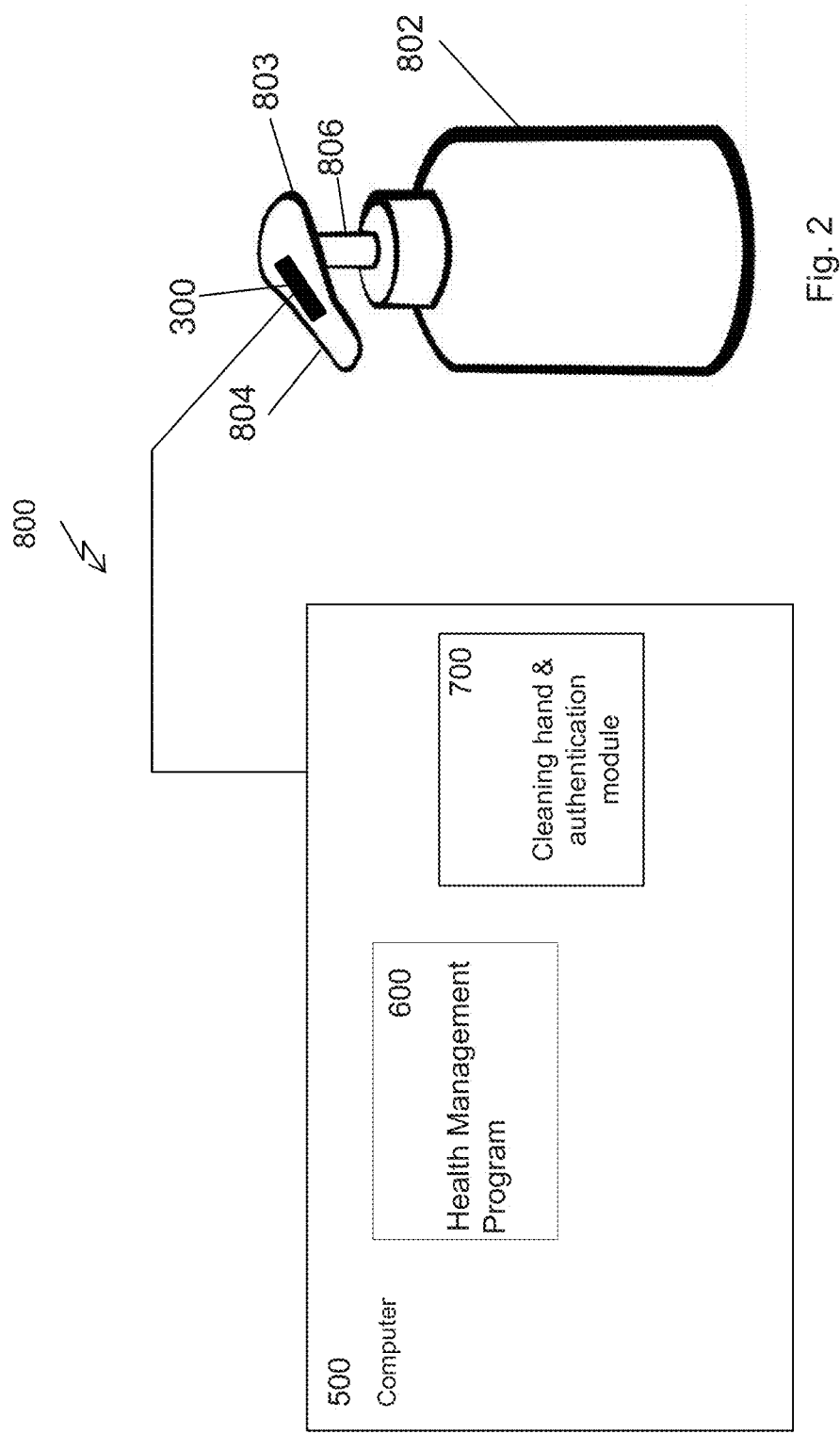
FIG. 2 illustrates a hand-hygiene system including a sanitizer dispenser with a manual dispensing mechanism in accordance with some embodiments of the present invention.

FIG. 2 illustrates a hand-hygiene system 800 including a sanitizer dispenser 802 with a manual dispensing mechanism 803, sensing unit 300 and health management program 600 in accordance with some embodiments of the present invention.

Manual dispensing mechanism 803 comprises an arm/pump 804 connected to a tube 806 that runs into the sanitizer to be dispensed. In accordance with some embodiments of the present invention, every time dispensing mechanism 803 is activated, e.g., every time arm/pump 804 is pressed, sensing unit 300 sends a signal indicating that dispenser 800 was in use to health management program 600, 700 via wired communication, wireless communication, e.g., via Wi-Fi or Bluetooth, or a combination thereof.

In accordance with some embodiments of the present invention, sanitizer dispenser 200 may be an automatic dispenser and as such the sensing unit 300 may include a touch sensor, a motion sensor, a sound sensor, an acoustic sensor or any other type of electrical or magnetic switch operable to activate the motor of dispenser 200 and to send a signal to the computer via wired communication, wireless communication, e.g., via Wi-Fi or Bluetooth, or a combination thereof.

In accordance with some embodiments of the present invention, any time sanitizer dispenser 200 is being used, sensing unit 300 detects the release of a sanitizer and sends a signal to health management program 600, 700.

In accordance with some embodiments of the present invention, a touch sensor may be used for capturing a physical touch by a user, a motion sensor for sensing the presence of a hand below the dispenser, and a sound sensor for detecting human voices. An acoustical sensor may be associated with multiple predefined audio patterns such as (a) the audio of sanitizer drawn up the tube and (b) the audio of air drawn up the tube. Thus, an acoustic sensor provides a twofold advantage for indicating when a sanitizer is being released from the dispenser and for indicating when the dispenser is empt.

FIG. 3 shows cleaning hands and authentication module 700 in accordance with some embodiments of the present invention.

Upon receiving indication of a user trying to access a new patient file, the user is asked to cleanse his/her hands using sanitizer dispenser 200 that is connected to the computer [710].

Upon using sanitizer dispenser 200, a signal detected by sensing unit 300 is received via health management program 700 and the user is allowed to get an access to a consequent/new patient [720].

In accordance with some embodiments of the present invention, authenticating of said signal may include authenticating dispenser barcode or sensor ID number [730].

FIG. 4 shows Health management software 600 in accordance with some embodiments of the present invention.

Health management program 600 may enable the user to access into data files of consequent patients only after receiving a signal from cleaning hand & authentication module 700 indicating that the sanitizer dispenser 200 has been used, i.e., that the user has been washed his hands.

Any time the sanitizer dispenser is used, health management software 600 receives an indication from either cleaning hands & authentication module 700 or sensing unit 300 that the sanitizer disperser was in use [610].

Upon receiving such indication, health management software 600 enables the user to switch between patient records or start or end session of patient record [620].

Upon receiving such indication, health management software 600 further enables the user to update information on patient file [630].

Thus, health management program 600 is programmed so that no new patient file can be accessed (opened) for writing new data unless it receives a signal from sensing unit 300 indicating usage of sanitizer dispenser 200. This way, the health-care provider is obligated to wash his/her hands between taking care of patients in order to use the medical record software.

Hand-hygiene systems 100, 150 may be easily connected to any dispenser, whether manually operated or automatic, and to any computer, both desk computer and laptop.

For this reason, hand-hygiene system 100,150 may be used in hospital departments, in which the patient's data is entered to the medical record immediately after the patient is examined, and also in an outpatient clinic or an ambulatory setting, in which the physician enters the data after examining the patient and before receiving another patient.

In accordance with some embodiments of the present invention, hand-hygiene system 100, 150 of the present invention may not only make the performance of hand hygiene an obligatory action in between patients, but may also identify the health-care provider. Such feature of hand-hygiene system 100, 150 may be highly advantageous in hospital departments where numerous personnel use same computers.

To identify the health-care provider, hand-hygiene system 100, 150 may include at least one of the following:

a voice recognition system operable to identify the health-care provider utilizing sanitizer dispenser 200. The voice recognition system may be implemented in or near by sanitizer dispenser 200 and may transmit the detected signal to the corresponding computer for identifying and approving the health-care provider;

a barcode to be scanned by a smartphone to identify the health-care provider utilizing sanitizer dispenser 200. Sanitizer dispenser 200 may include a barcode to be scanned by a smartphone. The user may capture the barcode via his/her smartphone and transmit it to the corresponding computer for identifying and approving the health-care provider; and a scanner to scan a name tag of the health-care provider to identify the health-care provider utilizing sanitizer dispenser 200. Sanitizer dispenser 200 may include a scanner for scanning the user's barcode. The scanner transmits the scanned name tag to the corresponding computer for identifying and approving the health-care provider.

In accordance with some embodiments of the present invention, such sanitizers may be soaps, alcohol-based materials, or other antibacterial or germicidal materials.

Figure 5A:
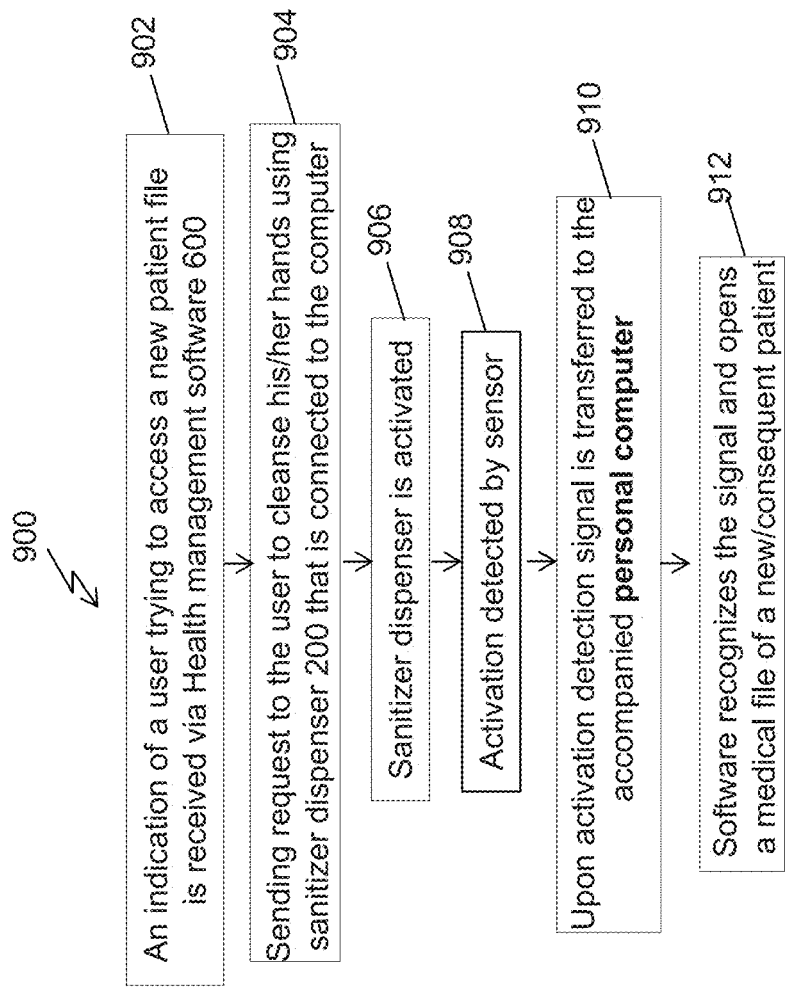
FIGS. 5A and 5B illustrate flowcharts of procedures to be carried out for ensuring that a medical personnel cleanses his/her hands prior to approaching a new/consequent patient in personal clinics and in multi-user departments in accordance with some embodiments of the present invention.
Figure 5B:
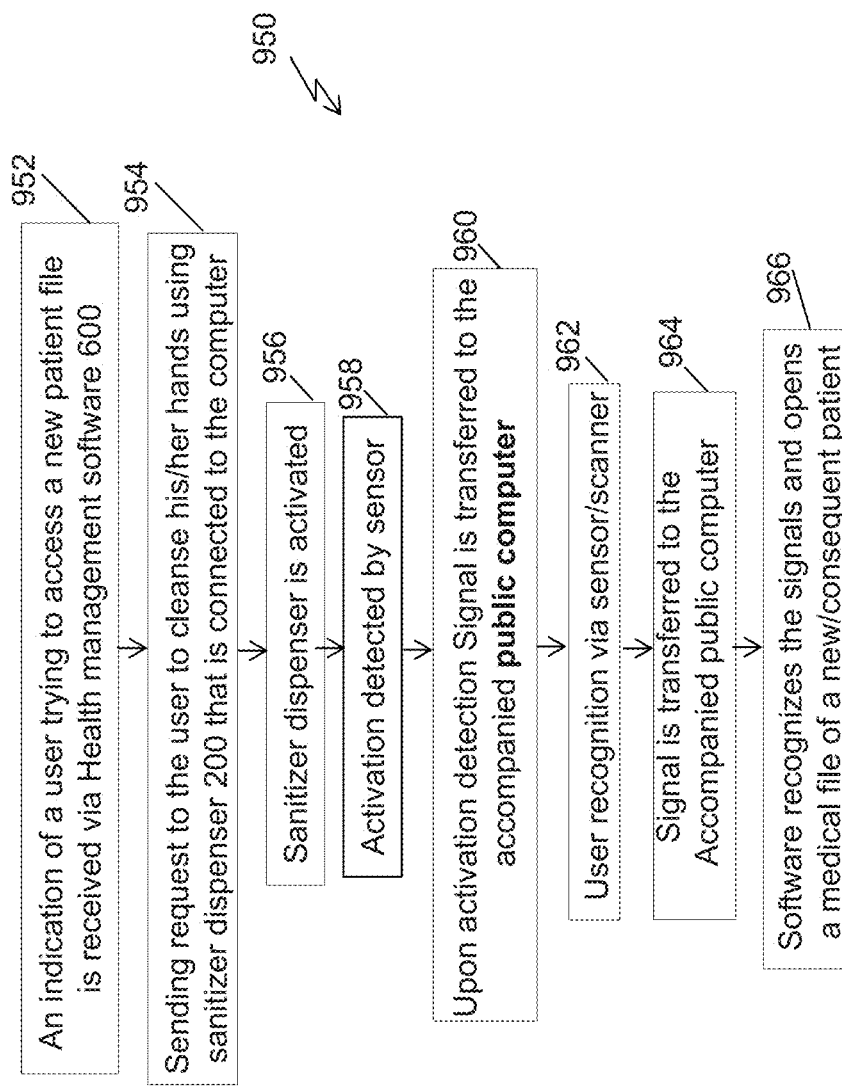

FIGS. 5A and 5B illustrate flowcharts 900, 950 of procedures that may be carried out for ensuring that the medical personnel cleanses his/her hands prior to approaching a new/consequent patient in personal clinics and in multi-user departments, such as hospital departments where numerous personnel use same computers, respectively.

The logic of flowchart 900 may be initiated when Health management software 600 receives an indication that a user is trying to access a new patient file, according to the block designated as 902. The user is then asked to cleanse his/her hands using sanitizer dispenser 200, according to the block designated as 904. The user cleanses his/her hands, i.e., activates sanitizer dispenser 200, according to the block designated as 906. The activation is detected by sensing unit 300, according to the block designated as 908.

The detected signal is transferred to the accompanied personal computer, according to the block designated as 910, and then, upon recognizing the signal, the software opens the medical file of a new/consequent patient, according to the block designated as 912.

The logic of flowchart 950 may be initiated when Health management software 600 receives an indication that a user is trying to access a new patient file, according to the block designated as 952. The user is then asked to cleanse his/her hands using sanitizer dispenser 200, according to the block designated as 954. The user cleanses his/her hands, i.e., activates sanitizer dispenser 200, according to the block designated as 956. The activation is detected by sensing unit 300, according to the block designated as 958.

The detected signal is transferred to the accompanied public computer, according to the block designated as 960, the user is being recognized via a sensor/scanner 400, according to the block designated as 962, sensor/scanner 400 transfers a signal to the accompanied public computer, according to the block designated as 964, upon recognizing the signal, the software opens the medical file of a new/consequent patient, according to the block designated as 966.

The system of the present invention may include, according to certain embodiments of the invention, machine readable memory containing or otherwise storing a program of instructions which, when executed by the machine, implements some or all of the apparatus, methods, features and functionalities of the invention shown and described herein. Alternatively or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention. Any of the teachings incorporated herein may wherever suitable operate on signals representative of physical objects or substances.

Unless specifically stated otherwise, as apparent from the following discussions, it is appreciated that throughout the specification discussions, utilizing terms such as, "processing", "computing", "estimating", "selecting", "ranking", "grading", "calculating", "determining", "generating", "reassessing", "classifying", "generating", "producing", "stereo-matching", "registering", "detecting", "associating", "superimposing", "obtaining" or the like, refer to the action and/or processes of a computer or computing system, or processor or similar electronic computing device, that manipulate and/or transform data represented as physical, such as electronic, quantities within the computing system's registers and/or memories, into other data similarly represented as physical quantities within the computing system's memories, registers or other such information storage, transmission or display devices. The term "computer" should be broadly construed to cover any kind of electronic device with data processing capabilities, including, by way of non-limiting example, personal computers, servers, computing system, communication devices, processors (e.g. digital signal processor (DSP), microcontrollers, field programmable gate array (FPGA), application specific integrated circuit (ASIC), etc.) and other electronic computing devices.

The present invention may be described, merely for clarity, in terms of terminology specific to particular programming languages, operating systems, browsers, system versions, individual products, and the like. It will be appreciated that this terminology is intended to convey general principles of operation clearly and briefly, by way of example, and is not intended to limit the scope of the invention to any particular programming language, operating system, browser, system version, or individual product.

It is appreciated that software components of the present invention including programs and data may, if desired, be implemented in ROM (read only memory) form including CD-ROMs, EPROMs and EEPROMs, or may be stored in any other suitable typically non-transitory computer-readable medium such as but not limited to disks of various kinds, cards of various kinds and RAMs. Components described herein as software may, alternatively, be implemented wholly or partly in hardware, if desired, using conventional techniques. Conversely, components described herein as hardware may, alternatively, be implemented wholly or partly in software, if desired, using conventional techniques.

Included in the scope of the present invention, inter alia, are electromagnetic signals carrying computer-readable instructions for performing any or all of the steps of any of the methods shown and described herein, in any suitable order; machine-readable instructions for performing any or all of the steps of any of the methods shown and described herein, in any suitable order; program storage devices readable by machine, tangibly embodying a program of instructions executable by the machine to perform any or all of the steps of any of the methods shown and described herein, in any suitable order; a computer program product comprising a computer useable medium having computer readable program code, such as executable code, having embodied therein, and/or including computer readable program code for performing, any or all of the steps of any of the methods shown and described herein, in any suitable order; any technical effects brought about by any or all of the steps of any of the methods shown and described herein, when performed in any suitable order; any suitable apparatus or device or combination of such, programmed to perform, alone or in combination, any or all of the steps of any of the methods shown and described herein, in any suitable order; electronic devices each including a processor and a cooperating input device and/or output device and operative to perform in software any steps shown and described herein; information storage devices or physical records, such as disks or hard drives, causing a computer or other device to be configured so as to carry out any or all of the steps of any of the methods shown and described herein, in any suitable order; a program pre-stored e.g. in memory or on an information network such as the Internet, before or after being downloaded, which embodies any or all of the steps of any of the methods shown and described herein, in any suitable order, and the method of uploading or downloading such, and a system including server/s and/or client/s for using such; and hardware which performs any or all of the steps of any of the methods shown and described herein, in any suitable order, either alone or in conjunction with software. Any computer-readable or machine-readable media described herein is intended to include non-transitory computer- or machine-readable media.

Any computations or other forms of analysis described herein may be performed by a suitable computerized method. Any step described herein may be computer-implemented. The invention shown and described herein may include (a) using a computerized method to identify a solution to any of the problems or for any of the objectives described herein, the solution optionally include at least one of a decision, an action, a product, a service or any other information described herein that impacts, in a positive manner, a problem or objectives described herein; and (b) outputting the solution.

The scope of the present invention is not limited to structures and functions specifically described herein and is also intended to include devices which have the capacity to yield a structure, or perform a function, described herein, such that even though users of the device may not use the capacity, they are, if they so desire, able to modify the device to obtain the structure or function.

Features of the present invention which are described in the context of separate embodiments may also be provided in combination in a single embodiment.

For example, a system embodiment is intended to include a corresponding process embodiment. Also, each system embodiment is intended to include a server-centered "view" or client centered "view", or "view" from any other node of the system, of the entire functionality of the system, computer-readable medium, apparatus, including only those functionalities performed at that server or client or node.

The invention claimed is:

1. A hand hygiene system comprising:
   a health management program including a cleaning hand module implemented on a processor; and
   a sanitizer dispenser equipped with a sensing unit that is associated with said processor via wired communication or wireless communication;
   wherein the sensing unit is configured to identify every time the dispenser is used and to transmit a signal to the health management program;
   wherein said health management program provides access to a new/consequent patient file only when receiving said signal;
   wherein the health management program is integrated with the sensing unit of the sanitizer dispenser by combining within the health management program a software driver related to the sensing unit, where once the software driver is incorporated, the health management program can detect operation of the sanitizer dispenser, at a stage of accessing a new patient file; and
   wherein the health management program is programmed so that no new patient file can be accessed for writing new data unless the health management program receives a signal from the sensing unit indicating usage of the sanitizer dispenser, the health management program identifying a health-care provider;
   wherein the health management program is programed to pop up a window, when a physician presses an open-new-file button to open a new patient's file, notifying that said sanitizer dispenser must be used to sanitize hands prior to opening a new patient's file; and
   wherein the health management program is programed to maintain the open-new-file button unresponsive until receiving a signal from said sensing unit indicating that the sanitizer dispenser has been used.

2. The hand hygiene system of claim 1, wherein said sensing unit comprises one of: a touch sensor, a motion sensor, a sound sensor, an acoustic sensor and an electrical or magnetic switch.

3. The hand hygiene system of claim 1, wherein said health management program closes said window and opens a new medical file when receiving a signal from said sensing unit.

4. The hand hygiene system of claim 1, wherein said sanitizer dispenser further comprising identification means selected from a barcode or a scanner.

5. The hand hygiene system of claim 1, wherein said sanitizer dispenser further comprising a module that includes an increasing counter indicating the number of times of using the sanitizer dispenser.

6. The hand hygiene system of claim 5, wherein when said counter is above a predefined threshold, the module provides an alert to replace the dispenser, and when said dispenser is replaced, said counter starts over.

7. The hand hygiene system of claim 1, wherein said sanitizer dispenser comprises (a) a reservoir to hold a sanitizer and (b) a dispensing mechanism selected from a mechanical, electrical, or mechanical-electrical dispensing mechanism.

8. A method for using the hand hygiene system of claim 1 implemented on a processor comprising the steps of:
- receiving an indication from a health management program that a user is trying to access a new/consequent patient file;
- sending request to the user to cleanse his/her hands using a sanitizer dispenser;
- in case of detecting the activation of said sanitizer dispenser, transferring a signal to said processor; and
- recognizing the signal and opening the medical file of a new /consequent patient.

9. A method for using the hand hygiene system of claim 1 implemented on a processor of a public remote computer comprising the steps of:
- receiving an indication from a health management program that a user is trying to access a new/consequent patient file;
- sending request to the user to identify himself/herself and to cleanse his/her hands using a sanitizer dispenser;
- in case of detecting the activation of said sanitizer dispenser and identifying the user, transferring a signal to the processor of the accompanied public computer, and recognizing the signal and opening the medical file of a new/consequent patient.

10. The method of claim 8, further comprising implementing a counter in said sanitizer dispenser for indicating the number of times of using the sanitizer dispenser.

11. The method of claim 10, further comprising providing an alert to replace the dispenser when said counter is above a predefined threshold.

12. The method of claim 1 further comprising a voice recognition system operable to identify the health-care provider utilizing sanitizer dispenser , where the voice recognition system is implemented in or near by sanitizer dispenser transmitting the detected signal to the corresponding computer for identifying and approving the health-care provider.

* * * * *

UNITED STATES PATENT AND TRADEMARK OFFICE
CERTIFICATE OF CORRECTION

| | | |
|---|---|---|
| PATENT NO. | : 11,749,385 B2 | Page 1 of 1 |
| APPLICATION NO. | : 16/503829 | |
| DATED | : September 5, 2023 | |
| INVENTOR(S) | : Ayelet Asif-Rosenberg et al. | |

It is certified that error appears in the above-identified patent and that said Letters Patent is hereby corrected as shown below:

On the Title Page

Item [60], insert:
--Provisional application No. 62/694,233, filed on July 5, 2018--

Signed and Sealed this
Twenty-fourth Day of October, 2023

Katherine Kelly Vidal
*Director of the United States Patent and Trademark Office*